United States Patent [19]

Sklar

[11] 4,044,122
[45] Aug. 23, 1977

[54] METHOD OF TREATING HERPES VIRUS HOMINIS INFECTIONS

[76] Inventor: S. Harvey Sklar, 647 Anderson Ave., Cliffside Park, N.J. 07010

[21] Appl. No.: 652,656

[22] Filed: Jan. 27, 1976

[51] Int. Cl.² ............................................. A61K 31/70
[52] U.S. Cl. .................................................... 424/180
[58] Field of Search ......................................... 424/180

[56] References Cited
PUBLICATIONS

Chemical Abstracts 63:4678h (1965).

Primary Examiner—Jerome D. Goldberg
Attorney, Agent, or Firm—Darby & Darby

[57] ABSTRACT

The method of treating herpes virus hominis infections in a mammal afflicted with said infections which comprises administering an effective amount of an alkali metal salt of adenylic acid.

17 Claims, No Drawings

METHOD OF TREATING HERPES VIRUS HOMINIS INFECTIONS

This invention relates to a method of treating herpes virus infections in mammals. More specifically, the invention pertains to the treatment of herpes virus hominis diseases in humans.

Herpes virus hominis (HVH) described a group of relatively large sized virus which are responsible for several diseases afflicting mammals, and humans in particular. It has recently been established that there are several strains of HVH virus. The type I strain commonly causes herpes labialis, while type II is generally recovered from genital lesions (herpes progenitalis) and transmitted venereally. Both of the preceding viral infections are characterized by the appearance on the skin or mucous membranes of single or multiple clusters of small vesicles perched on slightly raised inflammatory bases and containing a clear fluid. In females afflicted with herpes progenitalis, there may be no visible skin lesions, the infection remaining entirely within the vagina. In herpes labialis (commonly called herpes simplex) the vesicles are found on the mucous membranes of the cheek, lip and tongue. Herpes progenitalis lesions occur on, in and around the sexual organs and parts of both sexes. The vesicles are similar to those seen in herpes labialis and are usually discrete although occasionally several may become confluent. Chronicity and recurrence of the lesions are common features of this disease.

Herpes corneal dendritis is a superficial corneal ulceration caused by the herpes simplex virus. The disease is characterized by a branched lesion of the cornea, arranged like a series of interconnected canals, with knob-like terminals. Ulcerative keratitis is a serious corneal lesion resulting from herpes virus infection which may involve the stroma or depth of the cornea and lead to scarring, perforation and loss of vision. The dendritic variant is a superficial infection involving the nerve dendrites of the cornea.

Another more common infection caused by an HVH strain (herpes zoster) is shingles (acute posterior ganglionitis). This disorder is an acute infection of the central nervous system involving primarily the dorsal root ganglia and characterized by a vesicular eruption and neuralgic pain in the cutaneous areas supplied by the peripheral sensory nerves which arise in the afflicted root ganglia. The herpes zoster virus may attack the cranial nerves as well as those supplying the sensorium of the chest wall, abdomen, buttocks, thighs, legs and feet. Even after the vesicles characterizing the disease have become confluent and desquamated patients suffer from a post-herpes zoster neuralgia.

Although some drugs are currently available for treating HVH infections and their sequelae, they do not have broad spectrum effects and cannot be used to treat all of the HVH diseases. For example, Idoxuridine (2,-deoxy-5-iodouridine) has been found useful in the therapy of occular herpetic infection, but the compound has only limited efficacy in treating cutaneous herpes infestations and is not effective to treat herpes zoster. Similarly, corticosteroids may be given to alleviate the symptoms of herpes zoster but are not recommended for use in conjunction with occular herpes infections.

Recently, Fiala et al. (Journal of Infectious Diseases, Vol. 129, No. 1, January 1974) reported on the use of cytosine arabinoside and adenine arabinoside, in vitro, against herpes virus types I and II as well as varicella zoster virus. While the authors report generally favorable results, heteropolynucleotides and arabinosyl derivatives of nucleotides are cytotoxic anti-metabolites whole application to "in vivo" treatment must be limited due to their highly toxic properties.

It has now been unexpectedly discovered that the alkali metal salts of the monophosphoric derivative of adenosine (adenosine-5'-monophosphoric acid) or adenylic acid of the formula

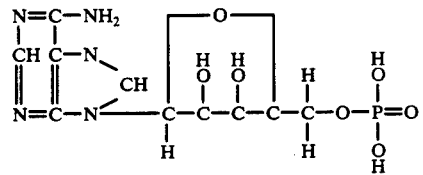

are effective in treating herpes virus hominis infestations in mammals.

More specifically, it has been found that the alkali metal salts of adenylic acid (adenosine phosphoric acid) may be administered to humans to treat herpes virus hominis infections.

Accordingly, one object of the present invention is to provide a method of treating herpes virus hominis infections in mammals.

A further object of the present invention is to provide a method of treating herpes virus hominis infections in humans by administering an effective amount of a pharmaceutically acceptable alkali metal salt of adenylic acid.

A still further object of the present invention is to provide a method of treating herpes virus hominis infections with the sodium salt of adenylic acid.

These and other objects of the present invention will become apparent from the following specification.

A molecule of adenylic acid [1] contains a purine (adenine), a 5 carbon sugar (ribose) and one phosphoric acid radical attached to the fifth ribose carbon. The molecular formula of adenylic acid is $C_{10}H_{14}N_5O_7P$ and the weight of the molecule is 347.23. Adenylic acid is available as a white crystalline material having a melting point of between about 196° and 200° C. and which is readily soluble in boiling water. Associated intimately with basic biochemical processes, adenylic acid is essential in phosphorylation reactions serving as energy transfer mechanisms and is also instrumental in several enzyme reactions as well as being necessary for carbohydrate and fat metabolism. Adenylic acid and its derivatives are also required for the transfer of high energy phosphate groups in connection with the oxidative utilization of glucose by the body's cells.

[1] Adenylic acid appears in the literature as adenosine-5'-monophosphate, adenosine, monophosphate, $A_5MP$, AMP, adenylic acid, muscle adenosine, ergodenylic and T-adenylic acid.

The alkali metal salts of adenylic acid (especially the sodium and potassium salts preferred for use herein) are stable in both the dry state and in solution. Accordingly, they may be stored as aqueous solutions in vials or ampules for relatively long periods without fear of decomposition. In the dry form the alkali metal salts of adenylic acid are extremely soluble in water to form solutions which may be administered orally (during which time they may be absorbed via the mucous membranes), parenterally (i.e., subcutaneously by intramuscular injection) or topically. The salts may be prepared from adenosine triphosphoric acid which occurs naturally in muscle tissue, or from yeast pursuant to known hydrolysis and separation procedures. In general, most processes precipitate adenosine triphosphoric acid with an alkaline earth metal base (e.g., barium hydroxide) which is hydrolyzed in an appropriate basic solution. The second or third phosphate radicals are removed during dydrolysis and precipitated as barium phosphate to leave a solution containing the barium salt of adenylic acid. The dissolved barium salt of adenylic acid is precipitated as the lead salt, the lead removed as a sulfide or sulfate leaving the adenylic acid in solution. Thereafter the adenylic acid is neutralized with sodium hydroxide, potassium hydroxide or an equivalent pharmaceutically acceptable alkali metal base and the solution sterilized or stored in ampules. If it is desired to obtain the dry form of the salt, the solution is evaporated to form a white crystalline material (sodium adenylate) which is separated and dried. Specific procedures and examples for the isolation of adenylic acid and the preparation of alkali metal salts of adenylic acid are well known in the art and described, for example, in U.S. Pat. Nos. 1,977,525, 1,976,175, 2,174,475, and 2,653,897, the disclosure of which are incorporated herein by reference. It should be understood that the alkali metal salt compounds useful in the invention may exist as either a mono or di-salt form depending upon the replacement by the metal of one or both of the hydrogens of the hydroxyl groups present in the terminal phosphoric acid radical.

The alkali metal salts of adenylic acid described herein, and in particular the sodium salt of adenylic acid, may be used to treat herpes virus hominis infestations in humans in a variety of dosage forms. The sodium salt of adenylic acid (hereinafter SAA) is commercially available as a sterile aqueous solution (containing 20 milligrams per cc.) suitable for topical and parenteral administration and in the form of 20 milligram tablets. The alkali metal salts of adenylic acid may also be administered topically or parenterally to treat herpes virus hominis infestation in humans in the form of an aqueous suspension or syrup formulation. In solid form, for oral administration the active ingredient may be contained in a capsule or given in the form of a powder or syrup.

Alternatively, the alkali metal adenylic acid salt may be supplied in a sustained dosage form which provides a prolonged therapeutic action in the body by preparing a gelatin solution of the acid salt having a pH within the range from about 5 to about 5.5. These gelatin solutions may be solid at body temperatures (up to 100° F) and liquified at higher temperatures, thus being suitable for parenteral administration (e.g., by intramuscular injection). The gelatin composition which normally contains an organic acid selected from the group consisting of polycarboxylic aliphatic acids and hydroxy aliphatic acids to adjust the pH to within the range from 5 to 5.5, generally will contain from 20 to 100 milligrams per cc. of adenosine phosphate (as the alkali metal salt). The preparation of adenylic acid salt gelatin solutions useful in the present invention is fully described in U.S. Pat. No. 2,653,901 the disclosure of which is incorporated herein by reference. As will be apparent to those skilled in the art, such compositions may be administered locally (as a topical medication), as well as parenterally.

The solid alkali metal adenylic acid salts of the present invention may be dissolved in sterile pyrogen-free distilled water to provide a minimum concentration of about 5 milligrams per cc. in aqueous solution, the preferably minimum concentration for administration in this invention. Preferably, the aqueous solutions of the present invention are prepared at the level of 20 milligrams per cc. of SAA acid. However, dilute aqueous solutions containing from about 5 to about 50 milligrams per cc. of SAA are adequate to provide satisfactory therapeutic effects in the present invention. The foregoing aqueous adenylic acid salt solutions may be administered parenterally (intramuscularly) or locally (topically) to treat herpes virus infestations. Any of the well known modes of local administration including spraying, douche, aerosol spray, and ointment formulations may be employed.

The sustained action gelatin solution of adenylic acid referred to herein usually contains from about 5 to about 100 milligrams per cc. of the alkali metal salt of adenylic acid. The concentration of adenylic acid and gelatin, the principle constituents of the composition, are not cirtical and concentrations as low as 5 milligrams per cc. of the adenylic acid salt are effective. The gelatin formulation is intended for intramuscular injection and is prepared so as to be readily liquifiable by warming to temperatures of about 100° F. In such instances the quantity of gelatin in the composition should not be so great as to prevent liquification of the solution at such temperatures. Preferably the gelatin solution will liquify at between about 100° and 150° F and contain from about 8 to about 20% gelatin (or about 180 milligrams per cc. of gelatin preferably for a solution containing 20 milligrams per cc. of SAA).

The adenylic acid salt-gelatin composition may be completely fluid, semi-solid or solid according to the environmental temperature. In the solid state it readily becomes fluid when the ampule in which it is contained is held in the hand or bathed in warm water, thus facilitating parenteral administration by injection. The needle and syringe used for parenteral administration should not be cold since this may cause the gelatin formulation to solidify prior to injection. The gelatin solution is readily injected as the liquid, and cools within the body to again solidify. In this manner the absorption of the salt of adenylic acid is slowed and the period of therapeutic action provided by the composition prolonged.

In most instances, an average daily dose of from about 5 to about 100 milligrams of the alkali metal salt of adenylic acid per day and preferably from about 5 to 50 milligrams per day has been found effective to treat HVH infestations in humans. The desired daily dose is preferably administered parenterally from an aqueous solution containing 20 milligrams/cc. of an adenylic acid (as the sodium salt) by intramuscular injection daily. Alternatively, the patient may receive a loading dose of 100 mg. of SAA in a gel formulation prepared, for example, according to Table 1, which is slowly released over a period of a day or more.

TABLE 1

| COMPOSITION PER CC. | [AQUEOUS] 20 MILLIGRAMS PER CC. | [GEL FORMULATION] | |
|---|---|---|---|
| | | 20 MILLIGRAMS PER CC. | 100 MILLIGRAMS PER CC. |
| Adenosine phosphate (as the sodium salt) | 20 mg. | 20 mg. | 100 mg. |
| Gelatin | | 180 mg. | 180 mg. |

TABLE 1-continued

| COMPOSITION PER CC. | [AQUEOUS] 20 MILLIGRAMS PER CC. | [GEL FORMULATION] 20 MILLIGRAMS PER CC. | 100 MILLIGRAMS PER CC. |
|---|---|---|---|
| Phenol | | 5 mg. | 5 mg. |
| Sodium Citrate | | for adjustment of pH | |
| Sterile Pyrogen-free Distilled Water q.s. ad | 1 cc. | | |

It will be appreciated that parenteral (intramuscular) administration of a 1 cc. dose of a 100 milligram per cc. SAA gel formulation of Table 1 can serve as a loading dose and will be released slowly over a period of time thereby permitting administration of medication less frequently to achieve the equivalent desired systemic drug titer as daily administration of a lower dosage of the aqueous solution. The quantity of active ingredient supplied by a given aqueous or gel formulation is relatively unimportant since the total dosage can be reached by administration of either one or a plurality of treatments at varying dosage levels. The preferable form of parenteral administration is by daily intramuscular injection of between 5 and 100 mgs. of SAA from a 20 milligram per cc. aqueous solution of SAA. Alternatively, SAA may be administered in the gelatin solution dosage form. The effective topical and parenteral dosage of the alkali metal adenylic acid salts for use in this invention and the frequency of treatment will vary depending upon the severity of condition, the stage and individual infective characteristics of each human being treated.

The following examples are illustrative of the method of preparing and utilizing alkali metal salts of adenylic acid in the present invention.

EXAMPLE I

A 20 milligram per cc. solution of the sodium salt of adenylic acid is prepared according to Example III in U.S. Pat. No. 2,653,897, labeled 20 milligrams per cc. aqueous SAA (sodium salt adenylic acid) and stored in 5 cc. vials.

EXAMPLE II

A gelatin solution of the sodium salt of adenylic acid is prepared pursuant to Example I in U.S. Pat. No. 2,653,901 and stored in ampules containing 5 ccs. of the 20 milligram per cc. gel and labeled 20 milligrams/cc. SAA gel. A 100 milligram per cc. gel formulation is also prepared pursuant to Example I of U.S. Pat. No. 2,653,901 and stored in 5 cc. ampules labeled 100 milligrams per cc. SAA gel.

EXAMPLE III

In clinical laboratory situations patients afflicted with various HVH infestations were treated wtih alkali metal salts of adenylic acid. The drug was administered in the form of an aqueous solution (20 milligrams per cc. SAA of the type prepared in Example I above) or in the form of a gel containing 100 milligrams per cc. adenylic acid as the sodium salt (100 milligrams/cc. SAA gel) prepared as in Example II above. Prior to administration the gelatin preparations were semi-solid at room temperature and were fluidized prior to injection by grasping the vial containing the medication by hand or placing the vial in hot water.

In most instances therapy consisted of parenteral administration of the aqueous solution on three consecutive days followed by injection of the adenylic acid gelatin composition on alternate days until remission was achieved. The quantity of drug administered during each treatment and the total dose were varied to meet the individual conditions of each patient. The following Table summarizes the diagnosis, treatment and results of each clinical case study.

TABLE 2

| PATIENT NO. | AGE | SEX | DIAGNOSIS | THERAPY | RESULTS |
|---|---|---|---|---|---|
| 1 | 7 yrs. | F | herpes-zoster (right buttock and lower abdomen) | 8 mg. aqueous SAA I.M.* repeated in 18 hours with 10 mgs. aqueous SAA - then 12 mgs. aqueous SAA I.M.** repeated five times on five alternate days | Rapid drying of vesicles - pain and discomfort improved by 3rd day after treatment commenced - complete remission |
| 2 | 68 | M | herpes-zoster (lesions left side of scalp including forehead and upper left eyelid) | 12 mgs. aqueous SAA I.M. followed by 20 mgs. aqueous SAA I.M. in 48 hours - then 8 treatments 100 mgs. SAA in gel***form I.M. per day, on alternate days | Therapy completed in three weeks - complete remission |
| 3 | 37 | M | post-herpes zoster neuralgia - constant pain and tenderness along nerve pathways (5th & 6th dermatomes-skin markings of recent herpes zoster lesions) | 1st day - 12 mgs. aqueous SAA I.M. - 2nd day 15 mgs. aqueous SAA I.M. 3rd day - 18 mgs. aqueous SAA I.M. - then ten treatments of 100 mgs. SAA gel I.M. on alternate days | Pain and discomfort relieved by 12th day and complete remission within 21 days after first treatment |
| 4 | 20 | F | Herpes labialis - confluent lesion and small vesicles on right side of mouth, corner, and adjacent upper lip | 1st day - 10 mgs. aqueous SAA I.M. 2nd day - 16 mgs. aqueous SAA I.M. 3rd day - 50 mgs. SAA gel I.M. Three treatments on alternate days of 100 mgs. SAA gel I.M. | Lesions dried in 48 hours and absorbed by 96 hours - complete recovery |
| 5 | 2½ | M | Herpes labialis - angle (left) mouth and adjacent cheek | 1st day - 12 mgs. aqueous SAA I.M. 2nd day - 12 mgs. aqueous | Lesions dried and crusting after 48 hours - all lesions disappeared |

TABLE 2-continued

| PATIENT NO. | AGE | SEX | DIAGNOSIS | THERAPY | RESULTS |
|---|---|---|---|---|---|
| 6 | 50 | F | Herpes labialis - recurring vesicles on lips with recent outbreak on tip of tongue | SAA I.M. 3rd-5th days - 8 mgs. aqueous SAA I.M. 1st day - 15 mgs. aqueous SAA I.M. 2nd-5th days - 20 mgs. aqueous SAA I.M. 7th day and following alternate days for 27 times - 100 mg. SAA gel. | and skin clear by last injection - complete remission No recurrence of lesions during therapy - complete remission |
| 7 | 80 | M | Herpes corneal ulcerative keratitis - small ground glass lesion about 2 millimeters (viewed with 20D lens) at 6 o'clock position in right eye - scar of old keratitic lesion also visible | Initial dose - 18 mgs. aqueous SAA I.M. 2nd day - 20 mgs. aqueous SAA I.M. 3rd day - 100 mgs. SAA gel I.M. and repeated 10 times on alternate days | Foggy vision substantially cleared after 3rd injection and completely cleared on 11th day - cornea crystal clear at termination of therapy - complete remission |
| 8 | 71 | M | Herpes corneal ulcerative keratitis - 2 millimeter corneal ulcer off center in left cornea | 12 mgs. aqueous SAA I.M. on 3 consecutive days and 15 mgs. aqueous SAA on 4th-11th day | Vision clearing on 3rd day - vision cleared and cornea crystal clear at conclusion of treatment - complete remission |
| 9 | 64 | M | Herpes corneal ulcerative keratitis - ulcer 0.5 millimeters off center on right cornea with hazy appearance of surrounding cornea (prior treatment with ara-a led to chronic corneal ulcer | 1st day - 14 mgs. aqueous SAA I.M. 2nd-4th days - 20 mgs. aqueous SAA I.M. 5th day - 100 mgs. SAA gel I.M. repeated 9 times on alternate days | Cornea clearing by 5th day and completely healed on 23rd day (successful corneal surgery done 3 months later and no recurrence on herpes lesions which are usually encountered after incomplete therapy |
| 10 | 20 | F | Herpes progenitalis - labia majora in adjacent perineum | 1st day - 14 mgs. aqueous SAA I.M. 3rd day - 20 mgs. aqueous SAA I.M. 5th day - 100 mgs. SAA gel I.M. - repeated 6 times on alternate days | All lesions gone 10 days after treatment - complete remission |
| 11 | 44 | F | Herpes progenitalis in labia majora and adjacent perineum - recurring monthly in conjunction with menstrual period | (Due to chronicity, therapy was planned for 6 months) 1st day - 14 mgs. aqueous SAA I.M. 3rd day - 18 mgs. aqueous SAA I.M. 5th day - 20 mgs. aqueous SAA I.M. 7th day - 100 mgs. SAA gel I.M. repeated 3 times a week on alternate days for 25 weeks | Pain and puriitis absent after 48 hours - lesions healed by 9th day - had 5 successive menstrual periods without outbreak of lesions - patient discharged - no reported outbreaks 2 months after treatment completed |
| 12 | 31 | M | Herpes progenitalis - vesicular eruption along shaft of penis and accessory recurrent lesions on lips and chin | 1st day - 14 mgs. aqueous SAA I.M. - repeated 48 hours later and then 100 mgs. SAA gel I.M. on alternate days repeated 9 times | Lesions healed in 72 hours |

*Treatment was administered on consecutive days unless otherwise indicated. Aqueous SAA refers to administration of the appropriate quantity of the sodium salt of adenylic acid from a stock sterile aqueous solution containing 20 mgs. of the salt per cc. of solution.
**I.M. refers to intramuscular injection.
***1 cc. SAA gel refers to administration of the sodium salt of adenylic acid in the form of a gel as in Example II above and containing 100 mgs. of the sodium salt of adenylic acid per cc. of solution.

While not wishing to ascribe any particular theory of operation to my invention, clinical investigation has revealed depressed nucleotide levels in the blood of individuals afflicted with HVH diseases. Shortly after commencement of therapy with an alkali metal salt of adenylic acid, the blood nucleotide titers have returned to normal levels. Stabilization of blood nucleotides at normal levels generally coincide with clinical remission from the HVH disorder with which a patient is afflicted.

A further advantage of the present invention is the fact that no instances of post-herpetic neuralgia (a common sequelae to herpes-zoster infection) have been observed in any subjects treated with SAA.

What is claimed is:

1. A method of treating herpes virus hominis infection in a mammal afflicted with said infection which comprises administering to said mammal an effective amount for treating herpes virus hominis of the sodium salt of adenylic acid.

2. The method according to claim 1 which comprises administering the salt of adenylic acid in the form of an aqueous solution.

3. The method according to claim 2 wherein the salt of adenylic acid is parenterally administered to said mammal.

4. The method according to claim 3 which comprises administering the salt by intramuscular injection.

5. The method according to claim 1 which comprises topically applying the salt to the infected area.

6. The method according to claim 5 wherein said effective amount for treating herpes virus hominis infections comprises from about 5 to about 100 milligrams per day of the salt of adenylic acid.

7. The method according to claim 6 wherein said effective amount comprises from about 5 to about 50 milligrams per day of the salt of adenylic acid.

8. The method according to claim 7 wherein said effective amount comprises 20 milligrams per day of the salt adenylic acid.

9. The method according to claim 2 which comprises administering the salt of adenylic acid in a gelatin solution.

10. The method according to claim 9 which comprises administering the salt of adenylic acid in gelatin to said human on alternate days.

11. A method of treating herpes simplex virus type I in a human afflicted with said virus which comprises parenterally administering to said human from about 5 to about 50 milligrams per day of the sodium salt of adenylic acid.

12. A method of treating an infection of herpes simplex virus type II in a human afflicted with said infection which comprises parenterally administering to said human from about 5 to about 50 milligrams per day of the sodium salt of adenylic acid.

13. A method of treating herpes zoster in a human afflicted with herpes zoster which comprises parenterally administering to said human from about 5 to about 50 milligrams per day of the sodium salt of adenylic acid.

14. A method of treating herpes corneal keratitis in a human afflicted with said condition which comprises parenterally administering to said human from about 5 to about 50 milligrams per day of the sodium salt of adenylic acid.

15. A method of treating herpes virus hominis infection in a mammal afflicted with said infection which comprises administering to said mammal an effective amount for treating herpes virus hominis of the potassium salt of adenylic acid.

16. The method according to claim 15 which comprises administering the salt in the form of an aqueous solution.

17. The method according to claim 16 wherein the salt is parenterally administered to said mammal.

* * * * *